United States Patent [19]
Mack et al.

[11] Patent Number: 5,457,248
[45] Date of Patent: Oct. 10, 1995

[54] BROMINATED DIPHENYLALKANE PRODUCTS AND PROCESSES

[75] Inventors: Arthur G. Mack, Lafayette; Rastko I. Mamuzic, West Lafayette; David C. Sanders, West Lafayette; Richard S. Rose, West Lafayette; Mary G. Harscher, Lafayette, all of Ind.

[73] Assignee: Great Lakes Chemical Corp., West Lafayette, Ind.

[21] Appl. No.: 224,345

[22] Filed: Apr. 7, 1994

Related U.S. Application Data

[63] Continuation-in-part of Ser. No. 44,266, Apr. 7, 1993, abandoned.

[51] Int. Cl.⁶ .......................... C07C 17/06; C07C 25/00
[52] U.S. Cl. .......................... 570/206; 252/601; 252/608; 570/190; 570/192; 570/210; 570/211
[58] Field of Search ..................... 570/190, 192, 570/206, 210, 211; 521/50; 252/601, 609

[56] References Cited

U.S. PATENT DOCUMENTS

| | | | |
|---|---|---|---|
| 3,141,860 | 7/1964 | Sauer et al. | 570/192 |
| 3,250,739 | 5/1966 | Sauer et al. | 570/192 |
| 3,331,793 | 7/1967 | Kopetz et al. | 570/192 |
| 3,658,634 | 4/1972 | Yanagi et al. | 161/175 |
| 3,763,248 | 10/1973 | Mitchell | 570/206 |
| 3,787,512 | 1/1974 | Nelson | 585/426 |
| 3,875,249 | 4/1975 | Nelson | 570/192 |
| 3,883,481 | 5/1975 | Kopetz et al. | 570/192 |
| 3,965,197 | 6/1976 | Stepniczka | 570/192 |
| 4,001,375 | 3/1977 | Freedman et al. | 526/1 |
| 4,214,103 | 7/1980 | Garman et al. | 568/639 |
| 4,287,373 | 9/1981 | Garman et al. | 568/639 |
| 4,327,227 | 4/1982 | Ayres et al. | 586/639 |
| 4,623,583 | 11/1986 | Mischutin | 428/242 |
| 4,717,776 | 1/1988 | Brackenridge et al. | 568/637 |
| 4,740,629 | 4/1988 | Brackenridge et al. | 568/639 |
| 4,929,785 | 5/1990 | Hussain | 585/426 |
| 5,003,117 | 3/1991 | Hussain | 560/210 |
| 5,008,477 | 4/1991 | Hussain | 570/208 |
| 5,030,778 | 7/1991 | Ransford | 570/208 |
| 5,039,729 | 8/1991 | Brackenridge et al. | 524/412 |
| 5,041,687 | 8/1991 | McKinnie et al. | 568/592 |
| 5,055,235 | 10/1991 | Brackenridge et al. | 252/609 |
| 5,077,334 | 12/1991 | Hussain | 524/469 |
| 5,124,496 | 6/1992 | Templeton et al. | 570/210 |
| 5,136,107 | 8/1992 | Stephens et al. | 568/639 |

FOREIGN PATENT DOCUMENTS

| | | |
|---|---|---|
| 0489406 | 12/1990 | European Pat. Off. |
| 0469569 | 7/1991 | European Pat. Off. |
| 0502333 | 2/1992 | European Pat. Off. |
| 1127582 | 4/1962 | Germany |
| 1277831 | 6/1969 | Germany |
| 918722 | 9/1961 | United Kingdom |
| WO91/13915 | 3/1991 | WIPO |

*Primary Examiner*—Werren B. Lone
*Attorney, Agent, or Firm*—Woodard, Emhardt, Naughton, Moriarty & McNett

[57] ABSTRACT

Described are processes for preparing brominated diphenylalkane products which are far whiter than prior known brominated diphenylalkane products. The resultant white brominated diphenylalkane products also form a part of the present invention, as do formulations incorporating the white brominated diphenylalkane products, and articles prepared therefrom.

39 Claims, No Drawings

BROMINATED DIPHENYLALKANE PRODUCTS AND PROCESSES

REFERENCE TO RELATED APPLICATION

This is a continuation-in-part of U.S. patent application Ser. No. 08/044,266 filed Apr. 7, 1993, now abandoned.

BACKGROUND OF THE INVENTION

The present invention relates generally to brominated non-fused aromatic compounds and their use as flame retardants. More particular, the present invention relates to brominated diphenylalkane products that are useful as flame retardants.

Flame retardants are common additives to flammable materials such as polymers. For this reason, it is highly desirable that flame retardants be as white as possible. This enables the production of white polymer formulations. Additionally, even when preparing a colored polymer formulation, polymer formulators often desire that the flame retardant be white. This is so that the desired color can be reproducably obtained from batch to batch, and so that the color imparted to the formulation is due to the pigment selected rather than its combination with the color of the flame retardant.

Brominated diphenylalkanes are known to have flame retardant properties when admixed with flammable macromolecular materials such as polymers. However, to date, prior-reported highly brominated diphenylalkanes prepared using known techniques have not been very white, having Yellowness Indexes (ASTM D 1925-70) well above 10. This compares poorly to the colors of other, commercially available flame retardants, which routinely have Yellowness Indexes less than about 8. As a result, there is a strong need for brominated diphenylalakene products having dramatically improved color characteristics and for processes for their production. The present invention addresses these needs.

SUMMARY OF THE INVENTION

An important aspect of one preferred embodiment of the invention is the discovery of a process that can be used to prepare highly brominated diphenylalkane products that are far whiter (i.e. less yellow) than those obtainable by other known procedures. Accordingly, one preferred embodiment of the invention provides a process for improving the color of a brominated diphenylalkane product having 1 to about 10 carbon atoms in its alkylene bridge and an average bromine number of about 6 or more. The process includes the step of contacting the brominated diphenylalkane product with an aromatic solvent at a temperature above about 175° C. to achieve dissolution of the brominated diphenylalkane product in the aromatic solvent. The resulting solution is then cooled to precipitate the brominated diphenylalkane product which has an improved color. Surprisingly, this process has been found to be effective to prepare products having YID's within the range of less than about 8 from products originally having YID's well above this range. This dramatic reduction in YID (and increase in Whiteness Index) provides an unprecedented pure, white brominated diphenylalakane product.

Another preferred embodiment of the invention provides solid, particulate flame retardant brominated diphenylalkane having 1 to about 10 carbon atoms in its alkylene bridge and having an average bromine number of at least about 6 and a Yellowness Index (ASTM D 1925-70) of about 0 to 8.

Another preferred embodiment of the invention provides a solid, particulate flame retardant brominated diphenylalakane product having 1 to about 10 carbon atoms in its alkylene bridge, prepared by the bromination of a corresponding diphenylalkane to obtain an average bromine number of at least about 6 and being free from alkylene-bridge-brominated diphenylalkanes.

Another preferred embodiment of the invention provides A solid, particulate flame retardant brominated diphenylalkene product having 1 to about 10 carbon atoms in its alkylene bridge, having an average bromine number of at least about 9 and exhibiting substantially no decomposition upon melting.

The invention further provides a solid, particulate flame retardant brominated diphenylalkane product having 1 to about 10 carbon atoms in its alkylene bridge, having an average bromine number of at least about 9 and exhibiting substantially no evolution of HBr when heated to a temperature of 330° C.

Other preferred embodiments of the invention provide flame retarded formulations which include a flammable macromolecular material and a flame retarding amount of any one of the above noted flame retardants, and molded articles prepared from such formulations.

Still other preferred embodiments provide aqueous dispersions including water, an emulsifying agent, and any one of the above-noted flame retardants, as well as latex compositions incorporating such dispersions and useful as coatings or adhesives.

Additional preferred embodiments, features and advantages of the present invention will be apparent from the following description.

DESCRIPTION OF THE PREFERRED EMBODIMENT

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

I. BROMINATED DIPHENYLALKANE PREPARATION/CHARACTERIZATION

The present invention provides highly brominated diphenylalkane products having extraordinarily good color characteristics, as well as other physical and chemical attributes, which make them excellently suited for use as flame retardants for flammable macromolecular materials. The highly brominated diphenylalkanes of the invention have YID's dramatically superior to any previously known brominated diphenylalkanes. Further, preferred highly brominated diphenylalkanes of the invention are essentially free from bromines on the alkylene bridge and are highly thermally stable.

Preferred preparative processes of the invention involve the bromination of a diphenylalkane substrate in bromine. In this regard, the bromine employed in the bromination process can be but is not necessarily purified to remove organic impurities such as grease, oil and carbonyl-containing hydrocarbons, by means such as distillation or treatment with a concentrated mineral acid such as sulfuric acid. These and other modes of purifying bromine are well known to the ordinarily skilled artisan. Bromine of high purity is also available from commercial sources. However, in accordance with the invention it has been found unnecessary to employ highly purified bromine. Rather, even standard grades of bromine as available from commercial sources and containing substantial levels of impurities (well above 10 ppm) can be used to nevertheless achieve superior white products having high thermal stability, as further discussed below.

The amount of bromine used will depend upon several factors including the level of bromination desired and whether any other solvents are present. In preferred brominations with bromine as the sole solvent, a stoichiometric excess of bromine of at least about 100% is employed (i.e. at least double the amount of bromine which is stoichiometrically required to achieve the desired level of ar-bromination is employed).

The diphenylalkane substrate employed in the bromination procedure can be completely unbrominated, or can be partially brominated albeit to an extent less than that desired. In the preferred case of an unbrominated substrate starting material, the diphenylalkane will have the formula:

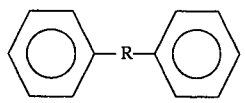

wherein R is an alkylene radical having from 1 to about 10 carbon atoms. Thus, suitable diphenylalkane reactants include diphenylmethane, 1,2-diphenylethane, 1,3-diphenylpropane, 1,4-diphenylbutane, 1,5-diphenylpentane, 1,6-diphenylhexane, 1,7-diphenylheptane, 1,8-diphenyloctane, 1,9-diphenylnonane, and 1,10-diphenyldecane. 1,2-diphenylethane (referred to herein sometimes simply as "diphenylethane") is a preferred diphenylalkane reactant. Like the bromine employed, the diphenylalkane substrate can be but is not necessarily highly purified: highly purified diphenylalkane substrates have been found to be unnecessary to produce the superior white products of the present invention.

Any suitable bromination catalyst can be employed which has sufficient catalytic activity to provide the level of bromination desired. Suitable bromination catalysts include aluminium catalyst such as aluminium powder and aluminium trihalides (e.g. $AlCl_3$ or $AlBr_3$), iron catalyst such as iron powder or iron trihalides (e.g. $FeCl_3$ or $FeBr_3$) antimony, zirconium, and the like. The bromination catalyst will be used in a catalytic amount. Usually about 0.1 to about 20 weight percent of catalyst is used relative to the weight of the diphenylalkane reactant, and more typically this value is about 1 to 10 percent.

Iron catalysts such as iron and iron salts, e.g. and iron trihalides, have been discovered to be highly advantageous catalysts for the bromination of diphenylalkane. Particularly, it has been discovered that those iron bromination catalysts do not cause bromination of the alkylene bridge of the diphenylalkane reactant. This provides access to highly improved flame retardants, since brominated diphenylalkane products having bromine on the alkylene bridge are more likely to cause degradation in polymer formulations and excessive evolution of HBr. In sharp contrast to iron catalysts such as iron powder or iron trihalide catalysts, catalyst systems which include aluminium powder or aluminium trihalide catalysts do cause substantial bromination of the alkylene bridge of diphenylalkanes, particularly at the carbons alpha to the phenyl groups. This leads to products with significant levels of alkylene-bridge-brominated diphenylalkanes, for instance undeca- and dodecabromodiphenylalkanes, which cannot thereafter be completely removed. Prior reported brominations of diphenylalkanes have generally employed catalyst systems including aluminium halide catalysts, but not iron catalysts, and there has been no appreciation prior to applicant's discoveries that iron or catalyzed bromination processes for diphenylalkanes unexpectedly provide particular advantage.

Generally, the diphenylalkanes substrate, bromine and catalyst can be contacted and reacted in any suitable fashion to provide the brominated diphenylalkane product. In a preferred mode of conducting the reaction, the bromine and bromination catalyst are charged to a reaction vessel and the diphenylalkane substrate, while in a molten state, is slowly added to the bromine and catalyst. While the molten diphenylalkane reactant may be maintained under an inert atmosphere such as nitrogen prior to feeding it to the reaction vessel, it has been found that this is not needed to provide superior products using preferred processes of the invention.

During the feed of the molten diphenylalkane to the bromine and catalyst, it is preferred that the bromine/catalyst mixture be maintained at a relatively low temperature, preferably below room temperature (i.e. about 25° C.) and more preferably about 15° C. or below, e.g. 0° C. to about 15° C. The feed of the molten diphenylalkane can be either subsurface or above surface. The superior, white products of the invention can be obtained by feeding the diphenylalkane in either manner. After the addition of the diphenylalkane reactant is complete, the bromination reaction is preferably conducted at a temperature of about 50° C. up to the reflux temperature of the reaction mixture, typically about 60° C.

The bromination reaction is conducted for a sufficient duration to achieve a brominated diphenylalkane product having an average bromine number of about 6 to 10, that is, having about 6 to 10 ar-bromines per molecule. Preferred such brominated diphenylalkane products will have the formula:

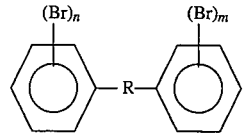

wherein R is an alkylene radical, n and m are each a number from 1 to 5, and n+m, on average, is in the range of about 6 to about 10. The level of bromination can be monitored by periodic sampling of the reaction products or, where nearly complete ar-bromination is desired, the completion of the reaction can be monitored by the termination of substantial slowing of HBr evolution.

The duration of the reaction will be dependent upon several factors such as the extent of bromination desired, the particular temperature and catalyst employed and the scale of the reaction. Typical reaction times will be in the range of about 1 to about 24 hours.

In a preferred aspect of the invention, the brominated diphenylalkane product will have an average bromine number of at least about 9 and will be predominatly (i.e. more than 50% by GC) comprised of decabromodiphenylalkane. More preferably, the product will be at least about 90% comprised of decabromodiphenylalkane; it is to be understood in this regard that higher levels of decabromodiphenylalkane, even those approaching 100% can be achieved, for instance by using longer reaction times. However, process economics often make it desirable to terminate the bromination reaction prior to achieving such high levels of the decabrominated product. Thus, lower brominated homologs can be present in the product in detectable amounts, usually mainly nonabromodiphenylalkane and octabromodiphenylalkane. Of these two lower brominated homologs, nonabromodiphenylalkane will usually be present in a greater amount.

The brominated diphenylalkane product can be isolated from the reaction mixture in any conventional manner. Preferably, the product is isolated by contacting the reaction mixture with hot water to distill of any excess bromine. For example, this may be accomplished by pumping the reacted mixture from the reaction vessel and into hot water to distill off any remaining bromine and leave the product in an aqueous slurry. When such a pumped transfer is contemplated, it is preferred to use a stoichiometric excess of bromine that will provide a pumpable medium upon completion of the reaction, for example an excess of 300% or 400% or more can be used. A metal chelating or complexing agent can be included in the water to aid in the removal of catalyst residues. Chelating or complexing agents have been found to improve the color characteristics of brominated diphenylalkanes prepared using both iron- and aluminium-based catalysts; however in the case of iron and iron trihalide catalysts, the color improvement (e.g. the level of reduction of YID) is dramatically greater than in the case of aluminium or aluminium halide catalysts. Suitable chelating or complexing agents include for example sodium gluconate, glycolic acid, EDTA and similar bidentate ligands.

The brominated diphenylalkane product can be recovered from the aqueous slurry by filtration and can be washed further with water or with organic solvents such as ketones, e.g. acetone, aromatics, e.g. toluene, halogenated alkanes, e.g. methylene dichloride, methylene dibromide, chloroform, bromoform and the like, which have also been found to improve the color characteristics of the product.

Brominated diphenylalkane products, especially those having alkylene-bridge-bromination (e.g. resulting from a bromination using an aluminum or aluminum trihalide catalyst), can be digested with a substances that is effective to react off or otherwise remove the aliphatically-attached bromines. For example, the product can be digested in a treatment solution containing a halogen reducing agent, e.g. an aqueous basic solution containing ammonia, hydrazine, organic amines and the like. For additional information as to suitable digestions effective for the removal of bromines which have replaced benzylic hydrogens as a result of a bromination process, reference can be made to International Publication No. WO 91/13915 (19 Sep. 1991, Great Lakes Chemical Corporation). As indicated above, when iron and iron halide catalysts are used as preferred, bromination of the alkylene bridge does not occur and thus, advantageously, such digestions are unnecessary for achieving products with very low hydrolyzable bromine content.

A feature of the present invention involves a high temperature aromatic solvent treatment of a brominated diphenylalkane to improve its color characteristics. Prior known methods for obtaining good color, including using purified bromine and/or purified substrate, and roasting of the product, have provided brominated diphenylalkane products with YID's well above 10 which have been reported in the literature. These products having YID's above 10 are off-white in color and confer poor color to white plastics in which they are formulated. Dramatically, the treatment of the present invention provides brominated diphenylalkane products having YID's in the range of about 1 to about 8, with YID's in the very low range of 1 to about 5 being readily obtained even after a singly treatment. Successive treatments may also be performed to further improve the purity and color of the product are thus products having YID's in the range of 0 to 8 are contemplated by the present invention.

The aromatic solvent used in the high temperature treatment of the present invention must not decompose at the temperatures at which the brominated diphenylalkane dissolves in the solvent. Typically, these temperatures will be in excess of about 175° C. and often in excess of about 200° C., e.g. usually about 200° C. to about 300° C. To perform the high temperature aromatic solvent treatment, the brominated diphenylalkane is contacted with the aromatic solvent at a temperature sufficiently high that the brominated diphenylalkane is dissolved in the solvent, preferably forming a solution essentially free of solid diphenylalkane material. This contacting step can be achieved by any suitable manner. In a preferred mode, the brominated diphenylalkane is slurried in the solvent at a temperature below that which is necessary to dissolved the brominated diphenylalkane, and the slurry is heated to the temperature sufficiently high to form a clear solution. For example, this may be accomplished by charging the brominated diphenylalkane to a vessel, and then charging the solvent to the vessel followed by the application of heat to the vessel.

Some aromatic solvent materials useful in this aspect of the invention, including preferred aromatic solvents, will be solids at ambient temperatures (i.e. about 20°–25° C.). When this is the case, the aromatic solvent material may be molten, and charged in the molten state to the vessel containing the brominated diphenylalkane. It will be understood that other modes of contacting the solvent and brominated product will be suitable, including for instance charging each to the reaction vessel prior to the application of heat or charging the brominated diphenylalkane materials to a reaction vessel containing the molten solvent. During the charge of brominated diphenylalkane to molten solvent, the solvent may be at a temperature which is either insufficient or sufficient to dissolve the brominated diphenylalkane.

Preferred aromatic solvents for use in this aspect of the invention are high-boiling aromatic compounds, so as to minimize or avoid the need to operate under pressure to achieve the high temperatures needed to effectively dissolve the brominated diphenylalkane. High-boiling aromatics with boiling points (at atmospheric pressure) above the highest treatment temperature utilized are preferred. These include, for example, non-fused aromatic compounds such as biphenyls, diphenylalkanes (e.g. with $C_1$ to $C_{10}$ alkylene bridges), diphenyloxides and diphenylsulfones, diphenylcarbonates, and the like, which are thermally stable at the high treatment temperatures employed, as well as fused aromatic solvents such as naphthalene or naphthalene derivatives, e.g. alkyl naphthalenes wherein the alkyl group or groups are typically $C_1$ to $C_5$ alkyls, e.g. methylnaphthalenes such as 2-methylnaphthalene. Mixtures of these materials are also suitable, such as may be found in certain Dowtherm heat transfer agents available from Dow Chemicals of Midland, Mich., for example Dowtherm A (a utectic mixture of biphenyl and diphenyloxide). Other Dowtherm products such as Dowtherm G (biphenyl phenyl ether) may also be used. Diphenylalkanes and diphenyloxide are preferred solvents, and in particular a diphenylalkane can be chosen to match the diphenylalkane substrate used to prepare the brominated diphenylalkane product.

The dissolution of the brominated diphenylalkane product is preferably achieved with agitation or stirring of the solvent/product mixture. Suitable decolorizing agents such as activated carbon may also be contacted with the solvent/product mixture and separated prior to precipitating the product.

After complete dissolution of the brominated diphenylalkane, the solution is caused to be at a temperature at which the brominated diphenylalkane precipitates. In this regard, the solution can be actively cooled to reduce temperature or may simply be allowed to cool on its own. It is preferable to apply cooling to the solution (as can be achieved in a heating/cooling jacketed vessel), as this results in smaller particle size upon precipitation of the brominated diphenylalkane. Unexpectedly, product recoveries are extraordinarily high, with recoveries of 75 wt % or more of the originally-charged brominated diphenylalkane product being readily obtained and ranging even up to about 90 to 95 wt % or more.

When the aromatic solvent employed is a solid at ambient temperature, it is preferred to hot-filter the product so as to avoid solidification of the solvent itself. Preferred hot filtrations will be conducted in the range of about 25° C. to about 100° C. depending on the particular solvent material involved. A hot filtration is not necessary, however, even when the solvent material is a solid at ambient temperatures. The solvent material and brominated diphenylalkane may both be allowed to solidify. The solid mixture can then be treated with another liquid organic solvent in which the solid solvent material but not the brominated diphenylalkane product is soluble. The brominated diphenylalkane product can then be filtered from the resulting medium.

After recovery, the solid brominated diphenylalkane is dried, usually at a temperature above about 100° C., to remove residual solvent. After drying, the solid brominated diphenylalkane product can be roasted or oven-aged at temperatures above about 200° C., but it has been found that this step is unnecessary to achieve excellent product color and thermal stability.

The brominated diphenylalkane product is preferably treated to reduce its particle size. For instance, the product can be mechanically ground or micronized, such as by air milling or similar known procedures.

Processes of the invention can be used to provide brominated diphenylalkane products with YID's (ASTM D 1925-70) below 8, far superior to those previously reported. Furthermore, products having YID's below about 5 are readily obtained. These preferred products have excellent thermal stability, for example as can be shown by thermogravimetric analysis (TGA). Products of the invention also have superior melting characteristics. Preferred decabromodiphenylethane products of the invention begin melting at temperatures above about 340° C., more preferably above about 345° C., and have DSC's above about 350° C. and generally in the range of about 350°–355° C. Preferred products of the invention undergo no substantial degradation upon melting, forming a clear, melted liquid as opposed to a brown liquid which is indicative of product decomposition.

Hydrolyzable bromine contents of preferred brominated diphenylalkane products are also very low, generally below 1000 ppm and typically in the range of about 100 ppm to about 250 ppm.

Upon heating, preferred products of the invention do not excessively evolve HBr. For instance, as demonstrated in the Examples below, preferred decabromodiphenylethane products show essentially no evolution of HBr at temperatures of about 330° and below, and only slight HBr evolution at a temperature of about 345° C. While the present invention is not limited by any theory, it is believed that these low levels of HBr evolution are due to the lack of bromination on the alkylene bridge of the brominated diphenylalkane.

II. FLAME RETARDED POLYMERIC FORMULATIONS

The brominated diphenylalkane products of the invention can be conventionally incorporated into flammable materials in flame retardant amounts. Generally, the flammable material will be a macromolecular material such as a polymer. Representative polymers in which products of the present invention may be used include polystyrene, including high impact polystyrene; copolymers of styrene; polycarbonates; polyurethanes; polyimides; polyamides; polyethers; acrylics; polyesters; epoxies; phenolices; elastomers such as butadiene/styrene copolymers and butadiene/acrylonitrile copolymers; terpolymers of acrylonitrile, butadiene and styrene (ABS); natural rubber; butyl rubber and polysiloxanes. Additional representative polymers include those of olefinically saturated monomers such as ethylene, propylene and butadiene; copolymers of two or more such alkylene monomers; copolymers of one or more such alkylene monomers, etc. Blends of polymers may also be used.

The amount of brominated diphenylalkane product necessary for flame retardancy will depend upon the particular brominated diphenylalkane employed and polymer material involved, as well as other flame retardants which might be included. Those of ordinary skill in the art will be readily able to incorporate an amount of the brominated diphenylalkane diphenylalkane which is necessary to achieve the desired level of flame retardancy. As is well known, it is preferred to incorporate the brominated flame retardant with another flame retardant material such as an inorganic compound, e.g. ferric oxide, zinc oxide, zinc borate, a group V element oxide such as a bismuth, arsenic, phosphorus or an antimony oxide. Of these, antimony oxide has long been used on the commercial scale and thus it is a preferred additional flame retardant. When an inorganic flame retardant is used in combination with the brominated diphenylalkane, the inorganic compound and brominated diphenylalkane will usually be present in a ratio of about 1:1 to about 1:10, more usually in the range of about 1:2 to about 1:4.

Generally speaking, polymer formulations contain up to about 40 wt % of the flame retardant system, whether it be the brominated diphenylalkane alone or its combination with another flame retardant. More typically, this range is about 10 to 30 wt %.

Polymer formulations incorporating flame retardants of the invention can be conventionally processed to form thermoplastic articles, for example by molding (e.g. injection, extrusion or compression molding). Depending on the particular application, the polymer formulation will contain further conventional additives such as pigments, fillers, UV stabilizers, plasticizers, antioxidants, and the like.

The invention provides high performance flame retardant resin systems with improved resistance to color shift on exposure to ultra violet light. As discussed above, preferred brominated diphenyl alkanes of the invention are far whiter (less yellow) than those obtained by other known procedures, having a yellowness index (ASTM D 1925-70) of about 0 to 8. Additionally, preferred flamed retardants of the invention are free from aliphatically-bond bromine. Bromines on the alkylene bridge of the diphenylalkane are far more susceptible to hydrolytic or thermal degradation than the bromine on the aromatic rings. Trace amounts of free bromine or HBr generated during compounding and processing can interfere with and/or inactivate the UV stabilization of hindered amine light stabilizers (HALS) such as Tinuvin 770 and Tinuvin 327. With the HALS inactivated, the resin systems will darken more rapidly upon UV exposure. In accordance with the invention, it has been found that preferred brominated diphenylalkane products which are free from alkylene bridge bromination and which have been subjected to high temperature solvent treatment ad discussed above can be used to prepare resin systems which highly resist color shifts on exposure to UV light.

For example, as demonstrated in Examples 10 and 11 below, formulations of high impact polystyrene and ABS incorporating decabromodiphenylethane (high temperature solvent treated, containing no detectable alkaylene bridge bromination) exhibited dramatically low color shifts upon exposure to UV light (ASTM D4459, 300 hrs.), giving Delta E values of less than 6 and typically in the range of about 3 to 6. Thermoplastic formulations are thus provided which are much more suited for applications in which color shift upon exposure to UV light is problematic.

The invention also provides high performance flame retardants and thermoplastic formulations with low corrosion properties. Formulated resin systems come in contact with metals throughout the formulation, compounding, molding and extrusion processes and in the case of wire and cable applications the formulated resin systems remain in intimate contact with various metals. These metals can include copper, mild steel and aluminum among others. The equipment used in processing the formulated systems is subject to corrosion from volatile bromine-containing species which may be present in the flame retardant at low levels or products due to decomposition of the flame retardant during processing. In the wire and cable industry there is a potential for corrosion to lead to loss of signal as well as a loss of the metal to resin interface which permits entrainment of moisture leading to further corrosion. Thus, the achievement of low-corrosion flame retardants and formulations is highly important to the polymer and other industries.

As demonstrated in Examples 12 and 13 below, thermoplastic formulations of the invention incorporating brominated diphenylalkanes essentially free of alkylene bridge bromination and subjected to high temperature solvent treatment as above, lead to significantly less corrosion than corresponding brominated diphenylalkanes containing alkylene bridge bromination and which are not subjected to the high temperature solvent treatment. In particular, a high temperature solvent-treated decabromodiphenyl ethane product free from alkylene bridge bromination, alone and in formulation, exhibited substantially no tendancy to corrode metal by contact or vapor emission. In contrast, a non-solvent-treated decabromodiphenylethane product containing alkylene bridge bromination tended to corrode metal alone or in formulation, which was evidenced by weight gain studies and visible pitting of metal samples.

III. AQUEOUS DISPERSION AND LATEX COMPOSITIONS

The invention also provides stable aqueous dispersions flame retardants, and coating and adhesive compositions, e.g. textile coatings, adhesives, caulks, sealants, and similar materials, which incorporate the aqueous dispersions. In this regard, the proliferation of water-based coatings and adhesives systems has led to the widespread use of a variety latex compositions incorporating dispersions of solid flame retardants.

Aqueous dispersions of this inventive embodiment employ a wetting agent to compatibilize the non-soluble flame retardant solid with water, and a protective colloid formed by a thickening agent to significantly slow sedimentation and stabilize the dispersion.

In accordance with the present invention the flame retardant employed is a brominated diphenylalkane product such as those described herein, having an average bromine number of at least about 6, preferably having a yellowness index of about 0 to about 8 and/or being free from alkylene bridge bromination. The brominated diphenylalkane is reduced to a submicron or micron particle size, preferably having an average particle size of 10 microns or less.

An inorganic flame retardant synergist can be used along with the brominated diphenylalkane. The synergist may be, for example, a metal oxide such as ferric oxide, zinc oxide, zinc borate, a group V element oxide such as a bismuth, arsenic, phosphorus or an antimony oxide. Of these, antimony oxide has long been used commercially and thus is preferred. When a synergist is used, the weight ratio of synergist to brominated diphenylalkane will usually be about 1:1 to about 1:10, more usually in the range of about 1:2 to about 1:5.

As examples, the wetting agent can be a nonionic wetting agent of the ethoxylated nonylphenol type, and the thickening agent can be hydroxy ethyl cellulose, carboxy methyl cellulose, methoxy or ethoxy cellulose, or the like. It will be understood however that a wide variety of wetting and thickening agents are known and their use in the present invention is well within the purview of one practiced in the area.

To prepare stable aqueous dispersions, the micropulverized brominated diphenylalkane flame retardant can first be dispersed in water containing the wetting agent, for example by gradual addition to an aqueous phase with strong agitation (e.g. by a high speed, high shear mixer). Thereafter, the resulting dispersion can be stabilized by adding small quantities of the thickening agent.

To prepare coatings or adhesives of the invention, the above-described aqueous dispersion, optionally after dilution, can be added to a polymer latex emulsion. Suitable polymers in the latex can be formed by polymerizing acrylic acid, methacrylic acid, acrylamide, methacrylamide, acrylonitrile, esters of acrylic and methacrylic acids, vinyl chloride, vinylidene chloride, styrene, butadiene, maleic or fumaric acids, and esters of same and the like. The polymer can be a homopolymer or copolymer of the above described monomers. Such emulsion polymers form films at room or elevated temperatures, alone or in the presence of plasticizers, and are commercially available or can be obtained by techniques well known to the art and literature.

Latexes such as those described above possess extremely good adhesive properties, and can be used in both coating and adhesive or bonding applications. One particularly preferred aspect of the invention is the use of coating compositions to coat textile materials in various forms such as staple, two, yarn, fiber, woven or non-woven fabrics, knits, carpets and the like. Fabric substrates can be of natural or synthetic origin, with synthetic fabrics such as nylon, polyester, acrylics, polypropylene and the like, more typically being used.

Textile materials will be coated with sufficient amounts of the coating compositions to provide the desired flame retardancy, and dried. These amounts will, of course, vary in accordance with the flammability characteristics of the textile materials themselves. Coatings formed in accordance with the invention have superior, white color, and resistance to color shift upon exposure to UV light, as demonstrated in the Examples below. For additional information as to stable aqueous dispersions and latex adhesive or coating compositions formed therefrom, reference can be made to U.S. Pat. No. 4,623,583.

To promote a further understanding of the invention and its advantages, the following Examples are provided. It will be understood that these Examples are illustrative and not limiting of the invention. Yellowness and Whiteness Indexes (YID's and WIE's) were obtained in accordance with ASTM D 1925-70 as specified in the 1990 Annual Book of ASTM Standards—Plastics, Volume 08.02 using a Color Gard System Model 2000/5 from Pacific Scientific. Melting point (M.P.) data were obtained using a Buchï Model 510 melting point apparatus. In M.P. determinations, products were initially heated at a rate of 5° C./min. to 300° C. and thereafter were heated at a rate of 1° C./min. To establish HBr evolution, a strip of pH paper was suspended above the sample during a melting point determination. A faint pink color on the pH paper indicated slight HBr evolution and a red color indicated heavy HBr evolution

EXAMPLE 1

Bromine (2397 g, 15.0 moles), (standard grade, Great Lakes Chemical Colo., El dorado, Ak.) was charged to a 2 L 4-necked reaction flask equipped with heated dropping funnel, stirrer and condenser followed by HBr trap. Molten diphenylalkane (DPE) (93.3 g, 0.517 moles) (unrecrystallized) was charged to the heated dropping funnel. Iron powder (1.82 g, 0.0326 moles) was added to the bromine in the reaction flask and stirred for 45 minutes. The DPE was slowly added to the reactor while maintaining the temperature between about 10° C. and 15° C. (HBr was evolved and trapped). Addition time of DPE was 60 minutes, and the reaction was then heated to reflux slowly over 90 minutes (58° C.). The reaction was maintained at reflux for 2 hours by which time HBr evolution was less than 0.3 g every 10 minutes. Heat was removed (cooled to 53° C.) and the product (in bromine) was pumped into water at 99° C. to remove the bromine (bromine collected in a Dean and Stark trap). The remaining slurry was filtered and washed with water (1 L de-ionized ("DI") water) and dried in an oven at 120° C. to a constant weight. 497.7 g (99.1% yield) of a tan solid were obtained with the following analysis ("Dodeca"= GC % dodecabromodiphenylethane, "deca"=GC % decabromodiphenylethane, etc.; "ND"=none detected):

| Analysis | Found | |
|---|---|---|
| % Organic Br | 81.76% | |
| Hydrolyzable Br | 1.603 | ppm |
| Fe ppm | 3282 | ppm |
| TGA 5% Wt loss | 325° | C. |
| YID | 73.4 | |
| Dodeca | ND | |
| Deca | 85.1% | |
| Nona | 13.5% | |
| Octa | 1.4% | |

EXAMPLES 2–4

Bromine (2418 g, 15.13 moles) was charged to a 2 L 4-necked reaction flask equipped with heated dropping funnel, stirrer and condenser followed by HBr trap. Molten DPE (94.4 g, 0.518 moles) (uncrystallized) was charged to the heated dropping funnel. Iron powder (0.91 g, 0.016 moles) (Aldrich) was added to reactor and reactor cooled with ice bath to 2° C. [Iron wire (0.2537 g, 0.0045 moles), was suspended just above the bromine level in reactor]. DPE was slowly added to the reactor while maintaining the temperature of reaction vessel contents between about 2° C. and 10° C. (HBr was evolved and trapped). After DPE addition was complete (60 minutes) the reaction was stirred 180 minutes and then heated to reflux slowly over 60 minutes (59° C.). The reaction was maintained at reflux for 7 hours, by which time HBr evolution was very slow. Heat was removed (cooled to room temperature) and the product (in bromine) was separated into three equal portions and pumped into hot water containing 1 wt % solutions of glycolic acid (Ex. 2), sodium gluconate (Ex. 3) and EDTA (Ex. 4) (bromine collected in Dean and Stark trap). The remaining slurries were filtered, washed with hot water, dried at 120° C., and then roasted at 200° C. for 30 minutes. All three samples were off-white solids with the following analysis:

Ex. 2

| Analysis | Found | |
|---|---|---|
| % Organic Br | 81.9% | |
| Hydrolyzable Br | 670 | ppm |
| Fe ppm | 15 | ppm |
| TGA 5% Wt loss | 335° | C. |
| YID | 14.8 | |
| Dodeca | ND | |
| Deca | 87.3% | |
| Nona | 11.9% | |
| Octa | 0.7% | |

Ex. 3

| Analysis | Found | |
|---|---|---|
| % Organic Br | 81.8% | |
| Hydrolyzable Br | 579 | ppm |
| Fe ppm | 15 | ppm |
| TGA 5% Wt loss | 327° | C. |
| YID | 16.1 | |
| Dodeca | ND | |
| Deca | 87.7% | |
| Nona | 11.5% | |
| Octa | 0.7% | |

Ex. 4

| Analysis | Found | |
|---|---|---|
| % Organic Br | 81.8% | |
| Hydrolyzable Br | 779 | ppm |
| Fe ppm | 15 | ppm |
| TGA 5% Wt loss | 334° | C. |
| YID | 16.1 | |
| Dodeca | ND | |
| Deca | 88.2% | |
| Nona | 11.1% | |
| Octa | 0.6% | |

EXAMPLE 5

Bromine (1934.4 g, 12.1 moles) (purified by distillation was charged to a 2 L 4-necked reaction flask equipped with heated dropping funnel, stirrer and condenser flowed by HBr trap. Molten DPE (75.0 g, 0.2077 moles) (Purified by recrystallization from MeOH) was charge to heated addition funnel. The reactor was cooled to 2° C. and FeCl$_3$ (4.3 g, 0.0265 moles) added. The DPE was added to the reactor while maintaining the temperature between about 0° C. and 10° C. (HBr was evolved and trapped). Addition time for the DPE was 34 minutes, after which the reaction was stirred for a further 20 minutes before heating to reflux (59° C.). The reaction was maintained at reflux for 9 hours. Heat was removed and the product (in bromine) was pumped into water at 99° C. to remove the bromine (bromine collected in Dean and Stark trap). The water (2 L) contained 17.3 g (0.079 moles) of sodium gluconate (Aldrich) to complex the iron catalyst. The remaining slurry was filtered and washed with water (3×350 ml de-ionized water) and dried in an oven at 120° C. for 14 hours. 388.4 g of an orange solid were obtained in the following analysis:

| Analysis | Found |
| --- | --- |
| % Organic Br | 81.2% |
| Hydrolyzable Br | 828 ppm |
| Fe ppm | <2 ppm |
| TGA 5% Wt loss | 325° C. |
| DSC | 350° C. |
| YID | 45 |
| Dodeca | ND |
| Deca | 92.3 |
| Nona | 6.0% |
| Octa | 1.8% |

EXAMPLE 6

High Temperature DPO Treatment

Crude decabromodiphenylethane product from Example 5 (50 g) was placed in a 500 ml 3 necked flask equipped with stirrer, thermometer and condenser. Diphenyloxide (135 g) was melted and added to the reactor and heat applied. At 228° C. the decabromodiphenylethane product dissolved to give a dark orange solution. The heat was removed and the product allowed to cool to 35° C. (precipitation started at 238° C). The crystals were filtered and the filter cake washed with methanol (3×50 ml). The solid was then re-slurried in methanol (150 ml) and the slurry warmed to reflux before filtering and washing with a further 25 ml of methanol. The white crystals were then dried in an oven at 120° C. overnight. 48.7 g of white crystals (97.4% recovery) were obtained with the following analysis:

| Analysis | Found |
| --- | --- |
| % Organic Br | 83.2% |
| Hydrolyzable Br | 237 ppm |
| Fe ppm | <2 ppm* |
| TGA 5% wt loss | 351° C. |
| DSC | 352.4° C. |
| YID | 4.8 |
| WIE | 73.7 |
| Dodeca | ND |
| Deca | 93.4 |
| Nona | 5.2% |
| Octa | 1.3% |

*Below detection limit

EXAMPLE 7

High Temperature DPE Treatment

Crude decabromodiphenylethane from Example 5 (50 g) was placed in a 500 ml 3 necked flask equipped with stirrer, thermometer and condenser. DPE (150 g) was melted and added to the reactor and heat applied. At 244° C. the decabromodiphenylethane dissolved to give a clear brown solution, and the temperature continued to rise to 251° C. Heat was removed and the product allowed to cool to 60° C. (precipitation started to form at 234° C.). The crystals were filtered and the filter cake washed with acetone (3×50 ml). The solid was then re-slurried in acetone (200 ml) and the slurry warmed to reflux before filtering and washing with a further 50 ml of acetone. The solid was then dried overnight in an oven at 120° C. 47.7 g of white crystals were obtained (95.4% recovery) with the following analysis:

| Analysis | Found |
| --- | --- |
| % Organic Br | 81.0% |
| Hydrolyzable Br | 164 ppm |
| Fe ppm | <2 ppm* |
| TGA 5% Wt loss | 350° C. |
| DSC | 354° C. |
| M.P. | 349–354° C.** |
| YID | 4.7 |
| WIE | 75.5 |
| Dodeca | ND |
| Deca | 94.4 |
| Nona | 4.3% |
| Octa | 1.3% |

*Below detection limit.
**Showed only slight HBr evolution only at 345° C. and above. Upon melting, product showed substantially no decomposition, forming a clear solution.

EXAMPLE 8

Nonpurified DPE/Bromine: High Temperature DPE Treatment

Bromine (2902 g, 18.16 moles) (standard grade) and iron powder (2.33 g, 0.0399 mole) were charged to a 2 L 4-necked reaction flask equipped with heated dropping funnel, stirrer and condenser followed by HBr trap. Molten DPE (111.2 g, 0.61 mole) (not recrystallized) was charged to the heated dropping funnel. DPE was added to the reactor while maintaining the temperature between about 2° C. and 6° C. (HBr was evolved and trapped). Addition time of DPE was 32 minutes, and the reaction was then heated to reflux slowly over 150 minutes (59° C.). The reaction was maintained at reflux for 3 hours, by which time HBr evolution had virtually ceased. Heat was removed and the product (in bromine) was pumped into water at 99° C. (2 L DI water containing 26.3 g sodium gluconate) to remove the bromine (bromine collected in Dean and Stark trap). The remaining slurry was filtered and washed with water (2 L DI water) and dried in oven at 120° C. for 1 hour. 593 g (100.% Yield) of a tan solid were obtained. The crude solid was charged into a 5 L reactor with DPE (1800 g, unrecrystallized) and the reactor heated with stirring. At 195° C. the color of the slurry turned markedly lighter. At 244° C. all of the decabromodiphenylethane product was in solution, and the reactor was allowed to cool (at 240° C. precipitate started to form). The precipitate was filtered when the temperature reached 70° C. through a preheated glass frit. The filter cake was washed with 1 L of acetone and then re-slurried with 600 ml of acetone and brought to reflux. The slurry was then filtered and then washed with a further 400 ml of acetone before drying in an oven at 120° C. overnight. Yield 535.5 g (90.4%). The crystals were then air milled (Fluid Energy Aljet Micro-jet, 4 inch model) to yield a fine white powder with the following analysis:

| Analysis | Found |
|---|---|
| % Organic Br | 83.6% |
| Hydrolyzable Br | 279 ppm |
| Fe ppm | <2 ppm |
| TGA 5% Wt loss | 351° C. |
| DSC | 350° C. |
| M.P. | 346–349° C.* |
| YID | 1.6 |
| WIE | 90.1 |
| Dodeca | ND |
| Deca | 89.4% |
| Nona | 8.5% |
| Octa | 2.2% |

*Showed only slight HBr evolution only at 345° C. and above. Upon melting, product showed substantially no decomposition, forming a clear solution.

EXAMPLE 9

Bromine (967.2 g) (Purified by distillation) was charged to a 2 L 4-necked reaction flask equipped with heated dropping funnel, stirrer and condenser flowed by HBr trap. Molten DPE (36.8 g) (Purified by recrystallization from MeOH) was charged to the heated addition funnel. The reactor was cooled to 0° C. and $AlCl_3$ (3.6 g) added. The DPE was then added to the reactor while maintaining the temperature between about 0° C. and 5° C. (HBr was evolved and trapped). Addition time for the DPE was 21 minutes, after which the reaction was heated slowly to reflux. The reaction was maintained at reflux for 5 hours. Heat was removed and the product (in bromine) was pumped into water at 99° C. to remove the bromine (bromine collected in Dean and Stark trap). The remaining slurry was filtered and the recovered product washed with water (3×200 ml DI water). The product was dried at 120° C. for 2 hours, washed with 2×1 L of toluene, dried in an oven at 120° C. for 14 hours and then roasted at 200° C. for 9 hours. The product had the following analysis:

| Analysis | Found |
|---|---|
| % Organic Br | 82.1% |
| Hydrolyzable Br | 9169 ppm |
| TGA 5% Wt loss | 340° C. |
| DSC | 348° C. |
| M.P. | 341–346* |
| YID | 10.0 |
| WIE | 61.7 |
| Dodeca | 1.1% |
| Deca | 94.6% |
| Nona | 4.9% |
| Octa | 0.4% |

*Heavy HBr evolution at 310° C. Upon melting, bubbles were observed and the product decomposed, forming a dark brown liquid.

EXAMPLE 10

Preparation of A UV Stable Flame Retardant HIPS

A decabromodiphenylethane flame retardant (FR) of the invention, prepared as above and bearing no bromines on the alkylene bridge (DBDPE), was formulated in HIPS (high impact polystyrene) as detailed below (percents given as percent of overall formulation) and injection molded to form plaques which were exposed in a Xenon Arc Weatherometer for 300 hours according to ASTM D 4459 (light exposure of plastics for indoor applications). The formulations passed the UL94 V-0 flammability test at 1/16". The color change from the initial formulation color after exposure is conventionally given as Delta E, with more desirable systems giving lower Delta E values. A decabromodiphenyl ethane product having trace levels of alkylene bridge bromination (DBDPE-ABB) was similarly formulated and tested. The results, set forth below, demonstrate dramatically low Delta E values for inventive formulations as compared to formulations incorporating decabromodiphenyl ethane products having even trace levels of alkylene bridge bromination.

|  | DBDPE | DBDPE-ABB |
|---|---|---|
| % Br | 10.4 | 10.4 |
| % FR | 12.8 | 12.8 |
| % ATO* | 3.2 | 3.2 |
| % Tinuvin 327 | 0.5 | 0.5 |
| % 944FL** | 0.5 | 0.5 |
| UL94, 1/16" | V-0 | V-0 |
| ASTMD4459 | 3.4 | 6.2 |

*ATO = antimony trioxide
**Chimassorb 944FL

The HIPS formulation with DBDPE had a starting YID of 7, which was visibly whiter than the HIPS formulated with the same pigment system but using DBDPE-ABB (YID=9). The latter is sufficiently more yellow as to require additional color pigment to mask the yellow cast for color matching in the non-UV stable HIPS. This need for additional pigments adds to the cost and further adjustments in the overall formulation to achieve the optimum physical properties.

EXAMPLE 11

Preparation of UV Stable Flame Retardant ABS

The DBDPE and DBDPE(ABB) were also compounded into ABS at load levels which gave V-0 flammability performance and tested for color stability according to the ASTM D 4459 for indoor applications. The results, set forth below, again demonstrate superior UV stability for the DBDPE formulation.

|  | DBDPE | DBDPE-ABB |
|---|---|---|
| % Br | 12.0 | 12.0 |
| % FR | 14.8 | 14.8 |
| % ATO* | 4.5 | 4.5 |
| % Tinuvin 327 | 0.5 | 0.5 |
| % 944FL** | 0.5 | 0.5 |
| UL94, 1/16" | V-0 | V-0 |
| ASTMD4459 | 5.3 | 7.2 |

*ATO = antimony trioxide
**Chimassorb 944FL

EXAMPLE 12

Corrosion Study By Vapor Exposure

Two pieces of steel shim 6" by 3" by 20 mils were cleaned with soap and water and rinsed with acetone. In a Brabender prepcenter mixing bowl at 200° C. was fluxing polypropylene homopolymer (Himont 6524) with 20% decabromodiphenyl ethane (DBDPE or DBDPE(ABB)) and 3.2% antimony trioxide. The weighed and cleaned shim stock was suspended in the vapors over the fluxing flame retarded polymer for 15 minutes. The exposed shim steel was then suspended in boiling water vapors for 30 minutes and then allowed to air dry at room temperature for one hour. The resulting shim stock was then weighted and visually inspected.

The formulation containing the DBDPE(ABB) gave a weight gain of 0.0009 for a 45.1366 gram steel shim and showed corrosion and pitting of the surface. In contrast, the formulation containing the DPDPE (no alkylene bridge bromination) gave no weight gain and no pitting or corrosion of the shim steel surface. The DBDPE thus exhibits a dramatically reduced tendency to corrode metals which is important to the preservation of processing equipment commonly used in compound operations.

EXAMPLE 13

Direct Metal Contact DBDPE Corrosion Study 1 gram of DBDPE(ABB) was placed on a cleaned carbon steel coupon (washed with soap and water, rinsed with acetone and air dried). The coupon was heated to 100° C. and held for one hour. The DBDPE was put through the same test protocol. At the end of one hour the flame retardant was shaken off the coupons and they were suspended over boiling water for one hour. Weights of the coupons were taken immediately after drying at room temperature and were again reweighted after one hour at room temperature.

The sample contacted with the DBDPE(ABB) gave a weight gain of 0.0010 on a 10.3081 gram coupon and was visibly corroded and pitted. The coupon contacted with the DBDPE showed no weight gain and no visible corrosion, again demonstrating the superior, non-corrosive nature of preferred FR's of the invention.

EXAMPLE 14

Preparation of Stable Aqueous Dispersion of Decabromodiphenylethane

A stable aqueous dispersion of decabromodiphenylethane and antimiony oxide was prepared using a lighthing mixer blade. A polypropylene beaker was charged with 23.7 parts by weight deionized water, 0.2 parts Rohm and Haas Tamol SN dispersant, and 0.8 parts surfactant (octylphenol capped with 30 moles of ethylene oxide). After mixing for 90 seconds at 1200 rpm, all components were fully solubilized. A total of 36 parts decabromodiphenylethane (average particle size 3–4 microns), prepared generally as in Example 8, was added slowly over the next three minutes under agitation. The mixture was then agitated another five minutes under the same conditions. The mixture was neutralized with 3 drops of 28% ammonium hydroxide solution. One part of 28% acrylic emulsion containing acidic functional groups was added as a thickener under agitation. A total of 0.5 parts of the 28% ammonium hydroxide was then added slowly, again under agitation. The resultant dispersion was placed into a sealed glass bottle for observation. After standing for one month at room temperature, no sediment was visible at the bottom of container (when inverted for observation). Additionally, there was no water layer on the surface. The dispersion thus had at least one month of shelf stability.

EXAMPLE 15

Coated Upholstery

In this example decabromodiphenylethane was compared to decabromodiphenyl oxide as a flame retardant in an automotive upholstery fabric backcoating. Two flame retardant dispersions were prepared as in Example 14, one containing decabromodiphenylethane and one containing decabromodiphenyl oxide substituted for decabromodiphenylethane. The particle size of the brominated diphenyl oxide averaged 3.5 microns and that of the brominated diphenylethane averaged 4.2 microns. The dispersions were added to an acrylic latex coating based predominatly upon butyl acrylate. Sufficient flame retardant dispersion was added to give 15% flame retardant (antimony oxide included) in the dry coating. These flame retarded coatings were applied to an 11 oz/yd$^2$ polyester automotive upholstery fabric also containing a small quantity of nylon reinforcement. After drying, the coating weight was calculated and the coated fabric was tested for flammability by Motor Vehicle Safety Standard 302 (MVSS-302). The results are set forth below (values given are char length, in inches):

| Coating (oz/yd$^2$) | DBDPE | DBDPO |
| --- | --- | --- |
| 1.5 | 1.5 | 1.5 |
| 2.0 | 1.4 | 1.3 |
| 3.0 | 1.1 | 1.0 |
| 3.5 | 0.9 | 0.8 |

These results indicate little if any difference in the performance of the two flame retardants, since slight differences may be attributed to the flame retardant particle size or a small difference in bromine content.

EXAMPLE 16

Color Stability of Coated Upholstery

In this example the superior color and color stability of coating compositions of the invention were demonstrated. DBDPE, prepared generally as in Example 8 and having an average particle size of 2.7 microns, a yellowness index of 2.5, less than 100 ppm bromine, and 229 ppm hydrolyzable bromine was used to prepare a dispersion as in Example 15. A sufficient, flame retarding quantity of the dispersion was added to a butyl acrylate based latex coating (also including ATO). The resultant coating had excellent color. The coating was applied to 6.5 oz/yd$^2$ automotive polyester fabric at a coating level of 2.1 oz/yd$^2$. The flame retardant component (DBDPE and ATO) comprised 25% by weight of the dry film, which was white i appearance. The dried coated fabric was heated for 9 minutes at 190° C., resulting in a relatively slight color change (Delta E=1.80).

All publications cited herein are hereby incorporated herein by reference as if fully set forth.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

What is claimed is:

1. A process for improving the color of a solid, brominated diphenylalkane product having 1 to about 10 carbon atoms in its alkylene bridge and an average bromine number of about 6 or more, comprising:

contacting the brominated diphenylalkane product with an aromatic solvent at a temperature above about 175° C. to achieve dissolution of the brominated diphenylalkane product in the aromatic solvent;

cooling the resulting solution to precipitate the brominated diphenylalkane product having an improved color; and recovering the brominated diphenylalkane product having a Yellowness Index (ASTM D 1925-70) less than 10.

2. The process of claim 1 which includes:

slurrying the solid, brominated diphenylalkane product in an aromatic solvent having a boiling point of at least about 200° C.;

heating the slurry to a temperature sufficiently high to achieve dissolution of the brominated diphenylalkane in the aromatic solvent;

maintaining the slurry at said temperature until the brominated diphenylalkane is substantially dissolved in the aromatic solvent; and cooling the solution after said maintaining, to precipitate the brominated diphenylalkane product.

3. The process of claim 2 comprising heating the slurry to a temperature of at least about 200° C.

4. The process of claim 3 wherein the brominated diphenylalkane is brominated diphenylethane.

5. The process of claim 3 wherein the brominated diphenylalkane product has been prepared by bromination of a diphenylalkane in bromine, in the presence of a bromination catalyst.

6. The process of claim 5 wherein the bromination catalyst is iron powder, $FeCl_3$ or $FeBr_3$.

7. The process of claim 5 wherein the brominated diphenylalkane product has an average bromine number of at least about 9.

8. The process of claim 7 wherein the brominated diphenylalkane is brominated diphenylethane.

9. The process of claim 8 wherein the brominated diphenylethane has an average bromine number of at least about 9.

10. The process of claim 9 wherein the brominated diphenylethane product is at least 80% comprised of decabromodiphenylethane.

11. The process of claim 10, wherein the aromatic solvent is a non-fused diaromatic compound having a boiling point of at least about 200° C.

12. The process of claim 11, wherein the aromatic solvent is diphenyloxide or diphenylalkane.

13. The process of claim 12 including isolating and drying the brominated diphenylethane whereafter it has a Yellowness Index (ASTM D 1925-70) less than about 8.

14. The process of claim 13 wherein the isolated, dried brominated diphenylethane has a Yellowness Index (ASTM D 1925-70) of less than about 5.

15. A solid, particulate flame retardant brominated diphenylalkane product having 1 to about 10 carbon atoms in its alkylene bridge, having an average bromine number of at least about 6 and a Yellowness Index (ASTM D 1925-70) of about 0 to less than 5.

16. The product of claim 15 wherein the brominated diphenylalkane product has a Yellowness Index (ASTM D 1925-70) in the range of about 1 to 5.

17. The product of claim 16 wherein the brominated diphenylalkane product has an average bromine number of at least about 9.

18. The product of claim 15 wherein the brominated diphenylalkane product is a brominated diphenylethane product.

19. The product of claim 16 wherein the brominated diphenylalkane product is a brominated diphenylethane product.

20. The product of claim 17 wherein the brominated diphenylalkane product is a brominated diphenylethane product.

21. The product of claim 20 wherein the product is at least about 80% comprised of decabromodiphenylethane.

22. The product of claim 21 wherein the product is at least about 90% comprised of decabromodiphenylethane.

23. A solid, particulate flame retardant brominated diphenylalkane product having 1 to about 10 carbon atoms in its alkylene bridge, prepared by the bromination of a corresponding diphenylalkane in the presence of an iron catalyst to obtain an average bromine number of at least about 6 and being essentially free from alkylene-bridge brominated diphenylalkane.

24. The product of claim 23 which has an average bromine number of at least about 9 and which is essentially free from undecabromodiphenylalkane and dodecabromodiphenylalkane.

25. The product of claim 23 which is a brominated diphenylethane product.

26. The product of claim 24 which is a brominated diphenylethane product.

27. The product of claim 26 which is at least about 80% comprised of decabromodiphenylethane.

28. The product of claim 27 which is at least about 90% comprised of decabromodiphenylethane.

29. A flame retarded formulation, comprising:

a flammable macromolecular material; and a flame retarding amount of a solid, particulate flame retardant brominated diphenylalkane product having 1 to about 10 carbon atoms in its alkylene bridge, having an average bromine number of at least about 6 and a Yellowness Index (ASTM D 1925-70) of about 0 to less than 5.

30. A flame retarded formulation, comprising:

a flammable macromolecular material; and a flame retarding amount of a solid, particulate flame retardant brominated diphenylalkane product having 1 to about 10 carbon atoms in its alkylene bridge, prepared by the bromination of a corresponding diphenylalkane in the presence of an iron catalyst to obtain an average bromine number of at least about 6 and being essentially free from alkylene-bridge brominated diphenylalkane.

31. A molded article comprising a flame retardant macromolecular formulation of claim 29.

32. A molded article comprising the flame retardant macromolecular formulation of claim 30.

33. A solid, particulate flame retardant brominated diphenylalkane product having 1 to about 10 carbon atoms in its alkylene bridge, having an average bromine number of at least about 9 and exhibiting substantially no decomposition upon melting.

34. A solid, particulate flame retardant brominated diphenylalkane product having 1 to about 10 carbon atoms in its alkylene bridge, having an average bromine number of at least about 9 and exhibiting substantially no evolution of HBr when heated to a temperature of 330° C.

35. A composition comprising an aqueous dispersion including water, a wetting agent, and a solid, particulate flame retardant of claims 15, 23, 33 or 34.

36. An adhesive or coating composition comprising a polymer latex emulsion incorporating a stable aqueous dispersion of claim 35.

37. A process for preparing a flame retardant brominated diphenylalkane product being essentially free from bromination on its alkylene bridge, comprising:

brominating a diphenylalkane having 1 to about 10 carbon atoms in its alkylene bridge in the presence of an iron bromination catalyst so as to produce a brominated diphenylalkane product having an average bromine number of at least about 6 and which is essentially free from alkylene-bridge bromination.

38. The flame retardant brominated diphenylalkane product of claim 33, said product further having a Yellowness Index (ASTM D 1925-70) of about 0 to about 10 and exhibiting substantially no evolution of HBr when heated to a temperature of 330° C.

39. The flame retardant brominated diphenylalkane product of claim 38, characterized in that it is produced by a process comprising:

brominating a diphenylalkane having 1 to 10 carbon atoms in its alkylene bridge in the presence of liquid bromine and an iron bromination catalyst to produce a brominated diphenylalkane product having an average bromine number of at least about 9;

contacting the brominated diphenylalkane product from said brominating step with an aromatic solvent at a temperature above about 175° C. to achieve dissolution of the brominated diphenylalkane product in the aromatic solvent;

cooling the solution resulting from said contacting step to precipitate the brominated diphenylalkane product; and recovering and drying the diphenylalkane product.

* * * * *

UNITED STATES PATENT AND TRADEMARK OFFICE
CERTIFICATE OF CORRECTION

PATENT NO. : 5,457,248
DATED : October 10, 1995
INVENTOR(S) : Arthur G. Mack, Rastko I. Mamuzic, David C. Sanders, Richard S. Rose, and Mary G. Harscher It is certified that error appears in the above-identified patent and that said Letters Patent is hereby corrected as shown below:

In column 1, line 14, please delete "particular" and insert in lieu thereof --particularly--.

In column 4, line 52, please delete "of" and insert in lieu thereof --or--.

In column 5, line 12, please delete "of" and insert in lieu thereof --off--.

In column 6, line 21, please delete "dissolved" and insert in lieu thereof --dissolve--.

In column 9, line 5, please delete "ad" and insert in lieu thereof --as--.

In column 9, line 42, please delete "diphenylalkanes" and insert in lieu thereof --diphenylethanes--.

In column 10, line 28, please delete "diphenylalkane" and insert in lieu thereof --diphenylethane--.

Also in column 10, line 52, please delete "two" and insert in lieu thereof --tow--.

In column 11, line 21, please delete "dorado" and insert in lieu thereof --Dorado--.

Also in column 11, line 24, please delete "diphenylalkane" and insert in lieu thereof --diphenylethane--.

In column 11, line 47 found within the table of Example 1, please delete "1.603" and insert in lieu thereof --1603--.

In column 14, line 35, please delete "2.33" and insert in lieu thereof --2.23--.

In column 15, line 55 found directly below the table of Example 9, please delete "tile" and insert in lieu thereof --the--.

UNITED STATES PATENT AND TRADEMARK OFFICE
CERTIFICATE OF CORRECTION

PATENT NO. : 5,457,248
DATED : October 10, 1995
INVENTOR(S) : Arthur G. Mack, Rastko I. Mamuzic, David C. Sanders, Richard S. Rose and Mary G. Harscher It is certified that error appears in the above-identified patent and that said Letters Patent is hereby corrected as shown below:

In column 18, line 3, please delete "predominatly" and insert in lieu thereof --predominantly--.

In column 18, line 41, please delete the "i" in between "white" and "appearance" and insert in lieu thereof --in--.

In column 19, lines 23-24, please delete "diphenylalkane" and insert in lieu thereof --diphenylethane--.

In column 9, line 39, please delete "diphenylalkanes" and insert in lieu thereof --diphenylethanes--.

Signed and Sealed this

Nineteenth Day of December, 1995

Attest:

BRUCE LEHMAN

Attesting Officer

Commissioner of Patents and Trademarks